United States Patent
Yang et al.

(10) Patent No.: US 12,291,716 B2
(45) Date of Patent: May 6, 2025

(54) PLANT THERMO-SENSITIVE MALE STERILE MUTANT tms15 AND USES THEREOF

(71) Applicant: Shanghai Normal University, Shanghai (CN)

(72) Inventors: Zhongnan Yang, Shanghai (CN); Jun Zhu, Shanghai (CN); Yu Han, Shanghai (CN)

(73) Assignee: Shanghai Normal University, Shanghai (CN)

( * ) Notice: Subject to any disclaimer, the term of this patent is extended or adjusted under 35 U.S.C. 154(b) by 103 days.

(21) Appl. No.: 18/084,433

(22) Filed: Dec. 19, 2022

(65) Prior Publication Data

US 2023/0272414 A1 Aug. 31, 2023

(30) Foreign Application Priority Data

Jan. 24, 2022 (CN) .......................... 202210081764.2

(51) Int. Cl.
*C12N 15/82* (2006.01)

(52) U.S. Cl.
CPC ..... *C12N 15/8289* (2013.01); *C12N 15/8237* (2013.01)

(58) Field of Classification Search
None
See application file for complete search history.

*Primary Examiner* — Brent T Page (57) ABSTRACT

The invention discloses a plant thermo-sensitive male sterile gene mutant tms15 and uses thereof. The nucleotide sequence of the plant thermo-sensitive male sterile gene mutant tms15 is SEQ ID No. 1. The inventor screened the thermo sensitive genic male sterile mutant tms15 by EMS mutagenesis of Zhonghua 11, which showed a male sterile phenotype under high temperature conditions (>28° C.) and restored fertility under low temperature conditions (22~24° C.). The cytological results shows that the sporogenous cells in tms15 plants proliferated excessively and the tapetum cells are also vacuolized abnormally under high temperature. The normal proliferation of sporogenous cells and the normal development of tapetal cells are restored to some extent after low temperature treatment.

5 Claims, 6 Drawing Sheets

Specification includes a Sequence Listing.

```
                             SEQUENCE LISTING

Sequence total quantity: 2
SEQ ID NO: 1            moltype = DNA  length = 3885
FEATURE                 Location/Qualifiers
source                  1..3885
                        mol_type = genomic DNA
                        organism = Oryza sativa
SEQUENCE: 1
atggtatcca atagtttctg gcttttcatc ctgctagtga gcttcatccc catttctgct   60
tgggcagaat cacgtgatat aagtactctg ttcactctga gggattcaat caccgaagga  120
aaaggctttc tccgtaactg gtttgattcg gaaactcccc catgcagctg gtcaggcata  180
acttgcatag gacataatgt tgtggcgatt gatttgtcct ctgttccact ctatgctccg  240
tttccattat gcattgggc attccagtca cttgttcggc tcaacttcag tggatgtgga   300
ttttccggag agcttccgga agctttggga aatttgcaga atctccagta cctagacttg  360
agcaataacg agcttactgg gccaatacct atctcactat ataacctgaa gatgctgaag  420
gaaatggtgc ttgactacaa ctccttgtca ggacaactta gtcctgctat tgctcagctg  480
cagcacctta ctaagctatc tatatccatg aattccatct ccggaagcct tccaccagat  540
ctgggcagcc tgaagaacct ggagttgttg gacattaaga tgaacacatt caatggatct  600
ataccagcaa cttttgggaa cctgtcttgt ctcttgcact ttgatgctag ccagaataac  660
ctaactggat caatattccc tggaataacc tcgttgacaa acctattgac acttgatcta  720
tcatcaaaca gttttgaggg aacaattcct agggagattg gtcaactgga aaatctggaa  780
ttactgattc taggaaagaa tgatctcact ggaaggattc cacaagagat tggtagtctg  840
aagcagctta agttacttca tctcgaggaa tgtcagttca caggcaaaat accttggtca  900
atcagtggac tcagcagctt gacagaactt gacatatcag ataacaactt tgacgctgag  960
ctcccatcat ccatgggtga gcttggcaat ctaacacagc tgattgcaaa gaatgctggg 1020
ctcagtggga acatgccaaa agaacttggg aattgcaaga agcttactgt tataaacctg 1080
tcattcaatg cccttattgg acctattcct gaagaatttg cagatttaga ggctattgtc 1140
tcattttttg tggaaggaaa taaactatcg ggtcgtgtcc cagattggat tcagaaatgg 1200
aaaaatgcaa ggtccatcag gttgggacag aacaaattca gtggaccttt gccagtgctg 1260
ccattgcagc atctgctaag tttcgctgca gaatccaacc ttctctcagg ttctatacct 1320
tctcacatat gccaagccaa ctccttgcat tcactcttat tgcatcataa caatctgact 1380
gggactattg atgaggcatt taaagggtgc acgaacctca ctgaattgaa cttgttagac 1440
aaccatattc atggggagga accaggatat ttagcagaat taccccctggt tactctggag 1500
ttgtcacaaa acaaattcgc agggatgtta cctgcggagc tgtgggagtc aaaaaccctt 1560
ctagagatat ctctcagtaa caatgaaatt accggcccaa tacctgagag tattggtaaa 1620
ctctctgtat tgcaaaggtt gcatatagac aataactttac tcgaagggcc tatccctcag 1680
tctgttggtg atctaaggaa tctgaccaat ctatccctgc gtggcaatag gttatctggg 1740
atcattccac tagcacttt caactgcgaa aaacttgcca cgctggactt gagctataac 1800
aatctgactg ggaacattcc aagtgccata tctcacttga cattgcttga tagcttgatt 1860
ttgtcttcca accagctgtc tggttctatc cctgctgaga tttgcgtggg atttgagaat 1920
gaggctcacc ctgactcaga gtttcttcag caccatggtc ttcttgatct gtcatacaac 1980
caattgagtg gtcagatccc aacatctata aagaactgtg caatggtagt ggtgctcaac 2040
ctccaaggca atttgctgaa tggcaccatt cctgtggagc ttggcgagct aacaaatctt 2100
acatccatta acttgtcatt taatgaattt gttggaccaa tgcttccatg gtctggacct 2160
ttggttcaat tgcaaggcct tattctgtcc aataaccacc tagatggctc cattcctgct 2220
aagataggcc aaatccttcc caaaattgca gtgctagact tgtcaagcaa tgcactcact 2280
ggcactctac cacagtcttt gctctgcaac aattacctaa accatctgga tgtcagcaac 2340
aaccacctat ctgggcatat ccagttctct tgccccgatg gcaaagaata ctcaagtaca 2400
ctgctcttct tcaattcaag cagcaaccat ttctcaggga gcctagatga gtctatctcg 2460
aactttcacac aattgtctac tcttgatatc cacaacaata gcctcactgg aaggttgcct 2520
tcagcacttt ctgatctcag ttctttgaat tatcttgatc tgtcgagcaa caatctctat 2580
ggtgccatac cctgtggaat ctgcaatata tttggcctct catttgccaa cttctcaggt 2640
aactatattg acatgtacag cttggcagat tgtgctgcag gaggcatttg ttctactaat 2700
ggtactgatc ataaagcatt gcatccatat catcgggttc gaagggcaat taccatctgt 2760
gcctttacat tcgtcatcat cattgttta gtgcttctgg ctgtttatct gagacggaag 2820
ctggttagaa gcaggccttt ggcttttgaa tctgccagta aggccaaggc tacagttgag 2880
cctacctcaa ctgatgaact gctaggaaag aagtcaaggg aacctctgag tatcaatctt 2940
gcaacatttg agcatgcact tctgagggtc accgcggatg atattctgaa agccacagaa 3000
aacttcagta aggtgcacat aataggtgat ggtggatttg gcactgtcta caaggcagcg 3060
ctccctgaag gccggagagt cgcgatcaag aggctccatg gtggccatca gttccaaggt 3120
gaccgtgagt ttctagctga gatggagaca attggaaagg tgaaacatcc aaacctcgtc 3180
cctctacttg gctactgtgt ttgtggcgat gaacgattcc tgatctacga gtacatggag 3240
aatgggagcc tcgagatgtg gctgagaaac cgagcagatg cacttgaagc tcttggatag 3300
ccggaccgtc tcaagatctg cctcggttca gcccgtgggc tcgccttcct gcatcatggc 3360
tttgtgcccc atatcatcca ccgggacatg aagtcgagca acattctact ggatgagaac 3420
ttcgagccga gggtctctga cttcggcctt gcaaggatca tcagtgcctg tgagacccat 3480
gtcagcactg acattgccgg tacatttgga tacattcctc ggagtatgg cctcacaatg 3540
aagtccacca cgaaaggcga cgtctacagc ttcggcgtcg tcatgctgga gctcctcacc 3600
ggacggccac ctacaggcca ggaggagtg caagggggtg gaaacctcgt cggctgggtg 3660
cggtggatga tcgcccgcgg taagcagaac gagctgttca tccatgctt gccggtttca 3720
agcgtgtggc gggagcagat ggcgcgcgtg ctcgccatcg cccgggactg caccgccgac 3780
gagccgttca agaggccgac aatgctggag gtggtgaagg ggctcaagat gacccacggc 3840
```

```
atggaatgtg gacctctggt ggtgaccgtc tccagggaca tgtaa                    3885

SEQ ID NO: 2           moltype = AA  length = 1294
FEATURE                Location/Qualifiers
source                 1..1294
                       mol_type = protein
                       organism = Oryza sativa
SEQUENCE: 2
MVSNSFWLFI LLVSFIPISA WAESRDISTL FTLRDSITEG KGFLRNWFDS ETPPCSWSGI    60
TCIGHNVVAI DLSSVPLYAP FPLCIGAFQS LVRLNFSGCG FSGELPEALG NLQNLQYLDL    120
SNNELTGPIP ISLYNLKMLK EMVLDYNSLS GQLSPAIAQL QHLTKLSISM NSISGSLPPD    180
LGSLKNLELL DIKMNTFNGS IPATFGNLSC LLHFDASQNN LTGSIFPGIT SLTNLLTLDL    240
SSNSFEGTIP REIGQLENLE LLILGKNDLT GRIPQEIGSL KQLKLLHLEE CQFTGKIPWS    300
ISGLSSLTEL DISDNNFDAE LPSSMGELGN LTQLIAKNAG LSGNMPKELG NCKKLTVINL    360
SFNALIGPIP EEFADLEAIV SFFVEGNKLS GRVPDWIQKW KNARSIRLGQ NKFSGPLPVL    420
PLQHLLSFAA ESNLLSGSIP SHICQANSLH SLLLHHNNLT GTIDEAFKGC TNLTELNLLD    480
NHIHGEEPGY LAELPLVTLE LSQNKFAGML PAELWESKTL LEISLSNNEI TGPIPESIGK    540
LSVLQRLHID NNLLEGPIPQ SVGDLRNLTN LSLRGNRLSG IIPLALFNCR KLATLDLSYN    600
NLTGNIPSAI SHLTLLDSLI LSSNQLSGSI PAEICVGFEN EAHPDSEFLQ HHGLLDLSYN    660
QLTGQIPTSI KNCAMVMVLN LQGNLLNGTI PVELGELTNL TSINLSFNEF VGPMLPWSGP    720
LVQLQGLILS NNHLDGSIPA KIGQILPKIA VLDLSSNALT GTLPQSLLCN NYLNHLDVSN    780
NHLSGHIQFS CPDGKEYSST LLFFNSSSNH FSGSLDESIS NFTQLSTLDI HNNSLTGRLP    840
SALSDLSSLN YLDLSSNNLY GAIPCGICNI FGLSFANFSG NYIDMYSLAD CAAGGICSTN    900
GTDHKALHPY HRVRRAITIC AFTFVIIIVL VLLAVYLRRK LVRSRPLAFE SASKAKATVE    960
PTSTDELLGK KSREPLSINL ATFEHALLRV TADDILKATE NFSKVHIIGD GGFGTVYKAA    1020
LPEGRRVAIK RLHGGHQFQG DREFLAEMET IGKVKHPNLV PLLGYCVCGD ERFLIYEYME    1080
NGSLEMWLRN RADALEALGW PDRLKICLGS ARGLAFLHHG FVPHIIHRDM KSSNILLDEN    1140
FEPRVSDFGL ARIISACETH VSTDIAGTFG YIPPEYGLTM KSTTKGDVYS FGVVMLELLT    1200
GRPPTGQEEV QGGGNLVGWV RWMIARGKQN ELFDPCLPVS SVWREQMARV LAIARDCTAD    1260
EPFKRPTMLE VVKGLKMTHG MECGPLVVTV SRDM                                1294
```

PLANT THERMO-SENSITIVE MALE STERILE MUTANT tms15 AND USES THEREOF

SEQUENCE LISTING

This application contains a Sequence Listing in form of XML electronically filed and hereby incorporated by reference into the specification in its entirety. The name of the XML file containing the Sequence Listing is SequenceListingXML. The size of the XML file is 7,964 bytes, and the XML file was created on Jan. 30, 2023.

CROSS-REFERENCE TO RELATED APPLICATION

This application claims all benefits accruing under 35 U.S.C. § 119 from China Patent Application No. 202210081764.2, filed on Jan. 14, 2022 in the China National Intellectual Property Administration, the content of which is hereby incorporated by reference.

FIELD

The invention relates to agricultural field, in particular to a plant thermo sensitive male sterile mutant and its application, which can restore fertility under specific conditions.

BACKGROUND

In agricultural production process, plant male sterility materials provide an important way and germplasm resources for the development of hybrid rice.

The photo thermo sensitive genic male sterile lines are mainly divided into photo sensitive, thermo sensitive and photo-thermo sensitive male sterile lines based on the environmental factors affecting them. There are many reports regarding the molecular mechanisms of fertility reversion in photo-thermo sensitive male sterile mutants, which are diverse. After the discovery of the photo-thermo sensitive male sterile line NK58S (Nongken 58S) in a *japonica* rice named NK58 (Nongken 58), all around the country have used NK58S for breeding in a large range and produced a number of male sterile varieties, including a indica rice named Peiai64S, which is widely used in two-line breeding (see Luo Xiaohe et al., 1992). Several photo thermo sensitive male sterile loci of rice have been reported in the past decade, and their molecular mechanisms have been elaborated:

Although breeding using two-line materials has great advantages compared with breeding of using three lines, it also faces some problems in production and uses. These problems mainly focus on that the fertility of two-line hybrid breeding is regulated by environmental factors, which is uncertain, leading to unstable seed production conditions, bringing risks to seed production, and greatly restricting the development of two-line breeding.

Photo-thermo sensitive genic male sterile lines are very important for two-line hybrid rice seed production. Although some light and thermo-sensitive genes in rice have been reported, only a few loci such as pms3 and tms5 have been widely used. Therefore, there need more photo-thermo sensitive genic male sterile gene to perform hybrid rice seed production.

SUMMARY

The inventor of this application conducted a large number of rice mutation experiments in the laboratory, among which, when using *japonica* rice Zhonghua 11 as the mutagenic material, it accidentally obtained a thermo-sensitive male sterile plant during screening through Ethylmethylsulfone (EMS) mutagenesis, and mapped the influencing gene TMS15 from the plant through BSA (Bulked segregant analysis) sequencing.

A further study of TMS15 showed that the change of its fertility is related to the integrity of the structure of the second layer of pollen exine. This gene encoded a leucine rich repeat receptor like kinase. In further research, the inventor accidentally obtained a thermo sensitive genic male sterile mutant tms15 during screening process. Under high temperature, the early development of male gametophytes in a plant containing the tms15 mutant (named as "tms15 plant" or "tms15 plants" below) will be disturbed and normal pollen could not be formed.

The fertility of tms15 plant is affected by different temperatures and can be restored under specific conditions. More importantly, the mutation site of the mutant is different from the reported photo thermo sensitive mutation site. Tms15 is a new thermo sensitive genic male sterile line germplasm resource. The analysis of tms15 temperature sensitive mechanism provides a molecular basis for further use of tms15 in two-line cross breeding.

Thus, in one aspect, the application provides a plant thermo-sensitive male sterile gene mutant tms15, wherein the nucleotide sequence of the plant thermo-sensitive male sterile gene mutant tms15 is SEQ ID No. 1.

In another aspect, the application provides an expression vector containing the plant thermo-sensitive male sterile gene mutant tms15 of claim 1.

In another aspect, the application provides a transgenic seed, wherein the genome of said transgenic seed comprises the plant thermo-sensitive male sterile gene mutant tms15.

In another aspect, the application provides use of the plant thermo-sensitive male sterile gene mutant tms15 in preparing of recessive genic male sterile transgenic plants.

Preferably, the plant thermo-sensitive male sterile gene mutant tms15 is used in plant breeding, wherein it includes:

(1) introducing the plant thermo-sensitive male sterile gene mutant tms15 into a target plant causing said plant sterility (such as, using a method of *Agrobacterium tumefaciens* inducting), the phenotype of which shows high temperature sterility and low temperature fertility recovery; and/or (2) using a sterile plant obtained in above step (1) as a female parent, using a another plant of another variety as a male parent to cross breeding, and cultivate a hybrid target plant, obtaining corresponding hybrid seeds.

In another aspect, the application provides a method for cultivating a fertility restorable plant whose pollen development is affected by temperature, wherein the method includes introducing the plant thermo-sensitive male sterile gene mutant tms15 into plant seed cells, and using the plant seeds that to conduct plant cultivation.

In another aspect, the application provides a method for regulating thermo-sensitive fertility traits of plants, wherein the method includes following steps: replacing TMS15 gene in wild type plants (such as rice or maize) with the nucleotide sequence of SEQ ID No. 1, or replacing the corresponding protein of TMS15 gene with the amino acid sequence of SEQ ID No. 2.

In another aspect, the application provides use of the plant thermo-sensitive male sterile gene mutant tms15, wherein it is used to regulate or provide the thermo-sensitive male sterile traits of plants, or used as a selection marker for transgenic plants.

Preferably, the selection marker has a feature of reversible change of the thermo-sensitive fertility. That is, it shows a character of fertility restoration under low temperature conditions; and shows a character of sterility under high temperature, when the selection marker is introduced into a plant.

In a preferred implementation mode, the nucleotide sequence of the plant thermo-sensitive male sterile gene mutant tms15 is SEQ ID No. 1.

The application also provides use of the plant thermo-sensitive male sterile gene mutant tms15 in plant breeding, the use includes:
(1) introducing the plant thermo-sensitive male sterile gene mutant tms15 into a target plant causing said plant sterility, the phenotype of which shows high temperature sterility and low temperature fertility recovery; and/or
(2) introducing the plant thermo-sensitive male sterile gene mutant tms15 into other plant varieties through hybridization, and the sterile plants obtained in F2 generation can also show the thermo-sensitive sterile phenotype;
(3) Or take the sterile plants obtained in (1) and (2) as the female parent, and use different plant varieties as the male parent to cross, cultivate hybrid target plants, obtaining corresponding hybrid seeds.

The application also provides a method for cultivating a fertility restorable plant whose pollen development is affected by temperature. The method includes importing the plant temperature sensitive male sterile gene mutant tms15 into plant seed cells, and using the plant seeds for corresponding plant cultivation.

The application also provides a method for regulating thermo-sensitive fertility traits of plants, wherein it includes the step of replacing specific glycine (G) in the N-terminal non catalytic active region of wild type TMS15 protein with (S).

The application also provides the use of the plant thermo-sensitive male sterile gene mutant tms15, wherein it is used to regulate or provide the thermo-sensitive male sterile traits of plants, or is used as a selection marker of transgenic plants.

TECHNICAL EFFECT

The mutant tms15 provided by the application can bring better sterility performance to plants, and the seed setting rate of plants that containing the mutant are obviously lower than those containing other thermo-sensitive sterile mutant. Applying the mutant tms15 to breeding process will yield higher breeding efficiency, and it will be easier to obtain high-purity sterile plants.

EXPLANATION OF FIGURES

FIG. 1 shows a phenotypic analysis result of WT and tms15 mutants under different environmental temperatures, wherein (A) shows phenotypic comparison of plants (rices) of wild type (WT) with tms15 plants under high temperature and tms15 plants treated under low temperature after heading; (B) shows phenotypes of spikelets of plants (rices) of wild type (WT) and tms15 plants at high temperature compared with those of tms15 plants at low temperature; (C) shows that under high temperature, the flowers and anthers of wild type (WT) stained s in a manner named Alexander staining and the pollen stained with iodine; (D) shows the flowers and anthers of tms15 plants (rices) stained in a manner named Alexander staining and pollen stained with iodine under high temperature; (E) Shows flowers and anthers of tms15 plants, under low temperature, stained in a manner named Alexander staining and pollen stained with iodine. Scale length is 20 cm in FIG. (A); 10 cm in FIG. (B); 2 mm for flowers, 200 for anther Alexander staining and pollen iodine staining μm in FIG. (C-E).

FIG. 2 shows SEM analysis of anther and pollen structure of Wild type (WT) and tms15 plants after treatment at different ambient temperatures. Wherein, under a scanning electron microscope, the morphology of WT and tms15 are shown in (A) and (F), anthers and their outer surface structures are shown in B and G, after high temperature treatment; the state of WT and tms15 anthers, after high temperature treatment, are respectively shown in C and H; Pollen of WT and enlarged view of pollen outer surface after high temperature treatment are are respectively shown in D and E; anthers and anther outer surface structure of rice containing tms15 mutant, after low temperature treatment, are respectively shown in I and J; the anther opening state of plant containing tms15 mutant after low temperature treatment is shown in K; the pollen of WT, after low temperature treatment, and its enlarged picture are respectively shown in L and M; wherein the scale length in the figures is 200 μM (in A, F, and I), 100 μM (in C, H and K), 5 μM (in B, D-E, G, J, and L-M).

FIG. 3 shows sections of tms15 plants treated at different ambient temperatures, in which, the semi thin section of WT anthers from stage 4 to stage 10 treated at 28° C. are shown in A-G; the section of tms15 anthers from the 4th to the 10th stage treated at 28° C. are shown in H—N; the section diagram of tms15 anthers from the fourth stage to the tenth stage treated at 22° C. are in O—U. In the FIG. 3, eMMC represents excessive proliferation of microspore mother cells; ISPC represents inner secondary parietal cell; MC represents meiotic cell; ML represents middle cell; MMC represents microspore mother cell; Msp represents microspore; OSPC represents outer secondary wall cell; PPC represents primary parietal cell; PSC represents primary sporogenous cell; SC represents sporogenous cell; T represents Felt layer; and Tds represents tetrad. The scale in this figure is 20 μm.

EMBODIMENT

The invention is described in detail below in combination with the drawings and the embodiments thereof, however the protection scope of the invention is not limited to the scope described in the embodiments.

The tms15 mutant is obtained as below.

The inventor uses *Oryza sativa* ssp. *japonica* (ZH11), a *japonica* rice variety, as materials, to screen thermo-sensitive male sterile mutants by ethyl methanesulfonate (EMS) mutagenesis. The mutagenesis and screening method of EMS mutants refers to an Article of Zhang et al. 2007. The M1 generation plants after mutation treatment are planted in the field. After the M1 generation normally bear seeds, the spikes with high seed setting rate of M1 generation are cut and the seeds for M2 generation are got. In the late spring and early summer of the next year, the seeds of M2 generation are planted, and the male sterile plants are screened under high temperature conditions. After the selected male sterile plants are cut, the seeds of them are naturally screened under low temperature conditions to observe the fertility recovery of each seed. The possible thermo-sensitive sterile plants are collected and the average seed setting rate is counted.

Through a large number of experiments, the inventor screened and obtained a thermo sensitive genic male sterile line, which was not found to be significantly different from Zhonghua 11 at the vegetative growth stage. Through sequencing verification, it is found that the gene sequence of the mutant contains tms15 mutant, and the gene sequence of the mutant tms15 is shown in SEQ ID No. 1 in the sequence list.

In the subsequent planting, the $F_2$ generation population was obtained by hybridizing a plant containing tms15 mutant (which is sterile under high temperature) with a Zhonghua 11 plant. After high temperature screening, $F_2$ populations were sampled according to the fertile and sterile phenotypes of the obtained plants, DNA of which was extracted for high-throughput sequencing, and the target gene TMS15 was cloned. Plant of Zhonghua 11 was used as recurrent parent, and plant containing tms15 mutant was used as female parent for hybridization until $BC_3F_2$ population was obtained for seed conservation and subsequent experiments.

High temperature environment treatment of rice plants was carried out in an artificial climate chamber, a glass greenhouse and a light incubator. The high temperature treatment condition is >28° C., the normal temperature condition is 22~24° C., and the lighting condition uses natural light or halogen light source.

Identification of Thermo-Sensitive Characteristics of Tms15

Figure 1:
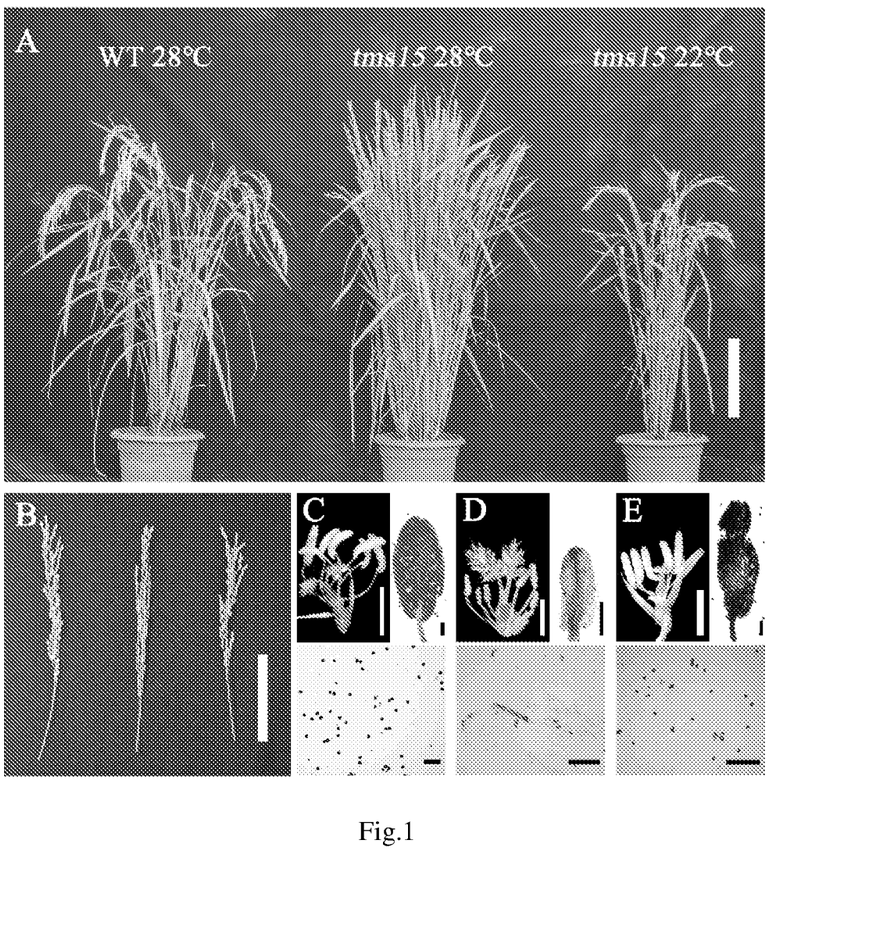

As shown in FIG. 1, under high temperature environment, the phenotype of tms15 plant is male sterile, no seed is produced, and its mature anthers are obviously shrunk and white (as shown in regions A-B in FIG. 1, the left side is wild type plant, the middle is the mutant plant treated by high temperature, and the right side is the mutant plant treated by low temperature). Alexander staining results showed that no pollen grains were formed in the mature anthers of the tms15 plants. After iodine staining of the anthers and their contents, only a few pollen residues were found therein, and no pollen was grained, but other structures were stained (region D in FIG. 1).

At the same time, the anthers of the wild type treated at high temperature were normal and yellow, and Alexander staining and iodine staining results showed that they contained mature pollen grains, which could normally produce seeds (regions B—C in FIG. 1).

The fertility of tms15 mutant plants treated at low temperature could recover normally, and there was no significant difference between anthers of tms15 plants and wild type plants. Alexander staining results showed that a large number of pollen grains were formed, and iodine staining results also showed that a large number of mature pollen grains in anthers could be stained (region E in FIG. 1). These results indicated that tms15 plants had a thermo sensitive male sterile phenotype.

The mature anthers of wild type and tms15 mutant plants at different environmental temperatures were observed by scanning electron microscopy (SEM) as well.

Figure 2:
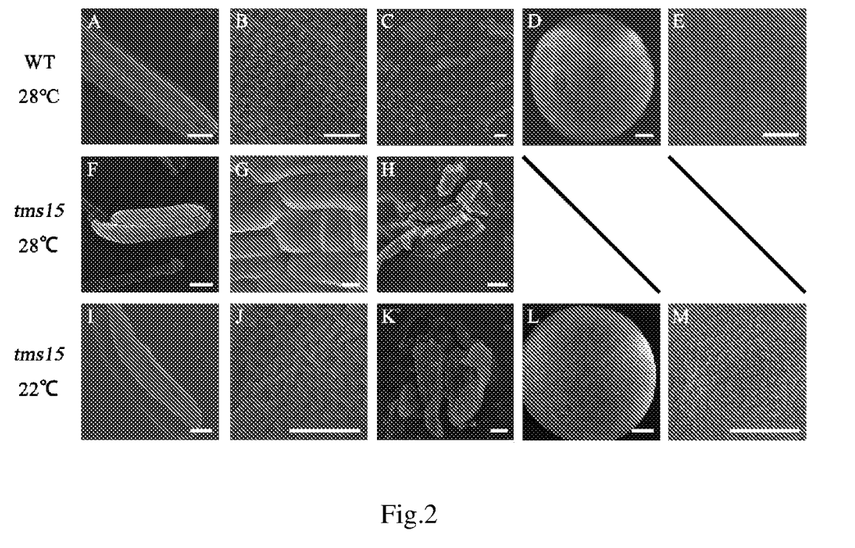

The results of SEM showed that anther length of tms15 mutant plants was significantly shortened under high temperature. The anther of tms15 mutant had no reticular structure like the wild type, and its surface had concave and was smooth. After the anther was opened, it was found that no pollen and other similar structures were released from anther of tms15 plants, while a large number of pollen grains were released from the wild type anther after it was opened. The pollen morphology and structure were normal, and its surface had a convex structure (as shown in regions A-E in FIG. 2).

The anther morphology of tms15 plant under low temperature treatment was not much different from that of wild type, and the outer surface of anther had the same reticular structure as that of wild type. After the anther was opened, it was found that there were pollen grains released, but the number was less than that of the wild type, and the surface of the pollen grains was basically the same as that of the wild type. This shows that high-temperature environment has a great impact on the development of anthers of tms15 (as shown in regions F-M in FIG. 2).

Cytological Analysis

Figure 3:
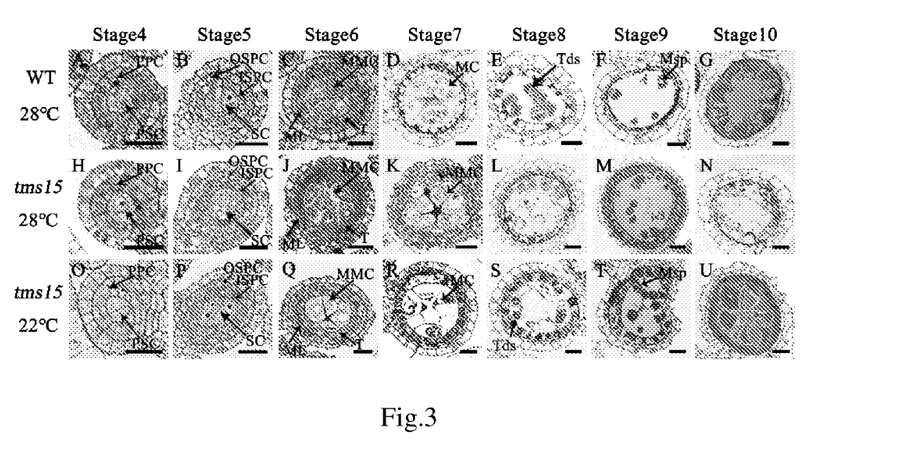

In order to further understand the defects of tms15 plants in the process of anther development, semi thin section experiments were conducted to check the anther development morphology of tms15 mutant plants at different temperatures. Compared with the wild type (WT in the figure), the anther sporogenous cells of tms15 plants under high temperature environment were not significantly different before the fifth stage. After entering the fifth stage, there were more sporogenous cells in the anther of tms15 plant than that of wild type, and the morphology of other parts of anther was the same as those of wild type. At the sixth stage, the anthers of tms15 mutant plant can normally form tapetum, and structure of their wall cell is the same as that of the wild type, but the number of microspore mother cells in the anther chamber is far greater than that of the wild type at the same stage, resulting in that they squeezed together. After entering the 7th stage, the number of microspore mother cells in anthers of tms15 mutant plant was still more than that of wild type. In the later period, the abnormal microspore mother cells in tms15 mutant plant could only continue mitose and could not complete meiotic process, and tapetum cells began to appear vacuolization, leading to cell degradation in the drug chamber. Under low temperature environment, the anthers of tms15 plants were not significantly different from those of wild type at each stage. It indicates that tms15 mutant plants appear proliferation disorder from sporogenesis stage, and the differentiation process of parietal cells are normal.

In order to observe the male fertility of tms15 mutants under different environmental temperatures, a batch of seeds containing tms15 mutants were germinated every week from May 18, and the last batch of seeds were germinated on July 27. The plants of Zhonghua 11 containing tms5 mutant were germinated as comparison. Each batch of plants was transplanted to the experimental base in Fengxian District of Shanghai after growing in an artificial environment for about 3 weeks. According to the average seed setting rate of plants germinated every week and the average temperature that week, a statistical chart was created with the germination date as the horizontal axis and the average seed setting rate of plants and the average temperature of the week, in which the plants boot, as the vertical axis (as shown in FIGS. 4 and 5).

Figure 4:
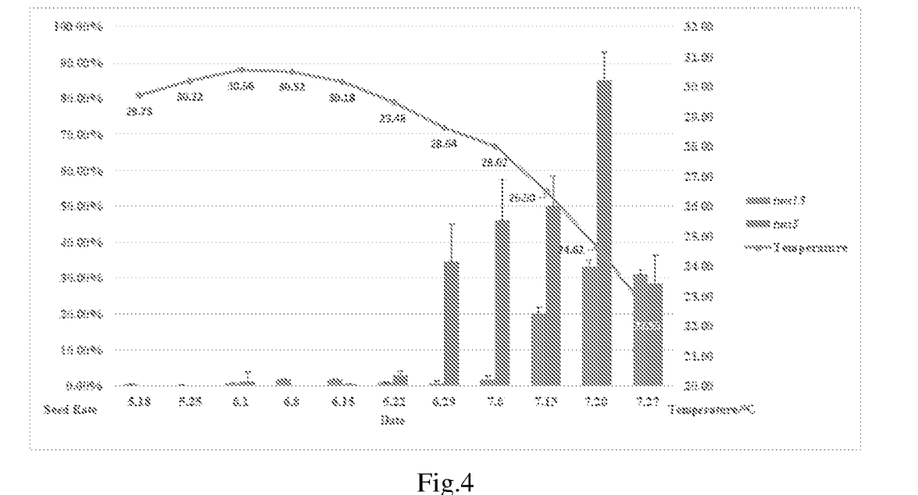
FIG. 4 shows a relationship between the seed setting rate of tms15 plants and the ambient temperature, which are planted in 2020.

As shown in FIG. 4, tms15 mutant plants and tms5 mutant plants germinated on Jun. 22, 2020 did not have obvious seed setting. The seed setting rate of tms5 mutant plants germinated during June 29 to July 20 increased with the decreasing temperature, and the maximum seed setting rate was more than 80%. Later, with the decrease of the average temperature during booting process, the seed setting rate also decreased sharply. But the seed setting rate of tms15 mutant plants did not increase significantly until July 13, and the seed setting rate was kept between 30% and 40%.

In FIG. 4, the horizontal ordinate represents the germination time of each batch of tms15 mutants plants. The left vertical ordinate represents the seed setting rate of tms15 and tms5 plants. Left column of the two parallel columns represents the seed setting rate of tms15, and right column of the two parallel columns represents the seed setting rate of tms5. The right vertical ordinate represents the average ambient temperature, and the green curve represents the average ambient temperature line of each week during booting.

Figure 5:
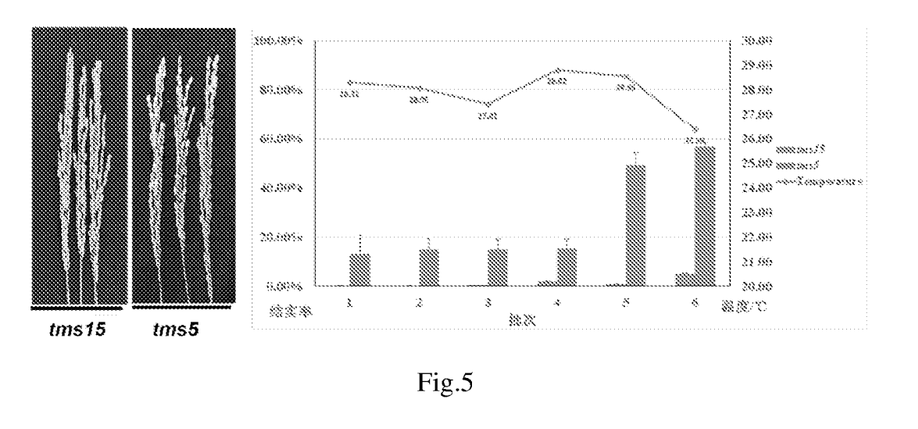
FIG. 5 shows the relationship between the seed setting rate of tms15 plants and the ambient temperature, which were planted in 2021.

As shown in FIG. 5, weekly average temperature in Shanghai in summer 2021 is affected by extreme weather, and there is no day above 29 degrees, leading to the self pollination seed setting rate of about 15% in the 1-4 batches of materials that should be sterile at high temperature for the most widely used tms5 plants, while the tms15 mutant has no obvious seed setting. Due to the short photoperiod and the gradual decrease of temperature, the fertility of tms5 began to recover at 26.39° C. in the last two batches, while the self setting rate of tms15 mutant was still only 6%. These results showed that tms15 plants had better sterility than zhonghua 11 containing tms5 mutant, and the fertility recovery temperature was lower than tms5 mutant. Therefore, the tms15 mutant provided by the invention can bring better sterility performance to plants. If it is used in breeding process, higher breeding efficiency will be obtained, and it will be easier to obtain high purity sterile plants.

TMS15 Gene Encodes an LRR-RLK Protein

In order to confirm whether the tms15 mutant is a thermo-sensitive male sterile mutant controlled by a nuclear gene, the tms15 mutant was used as a female parent to hybridize with Zhonghua 11 under high temperature, to obtain $F_1$ generation seeds. The obtained $F_1$ generation seeds were planted to obtain $F_2$ generation population. By counting the number of fertile plants (which number is 316) and sterile plants (which number is 95) of $F_2$ generation population under high temperature, chi square test was carried out to confirm that it conforms to Mendel's Law of Segregation, and the separation ratio of fertile plants and sterile plants is about 3:1 (Referring to Table 1). Therefore, tms15 mutant belongs to a thermo sensitive genic male sterile line controlled by a pair of recessive genes.

Below table 1 shows Chi square test results of $F_2$ generation fertility phenotype segregation obtained by hybridizing tms15 plants with plants of Zhonghua 11.

TABLE 1

| $F_2$ population of tms15 | Number of sterile plants | Number of fertile plants | Total number of plants | $\chi^2_{0.05}(3:1)$ |
|---|---|---|---|---|
| Theoretical value | 102.75 | 308.25 | 411 | 3.84 |
| Observed value | 95 | 316 | 411 | 0.68 |

Figure 6:
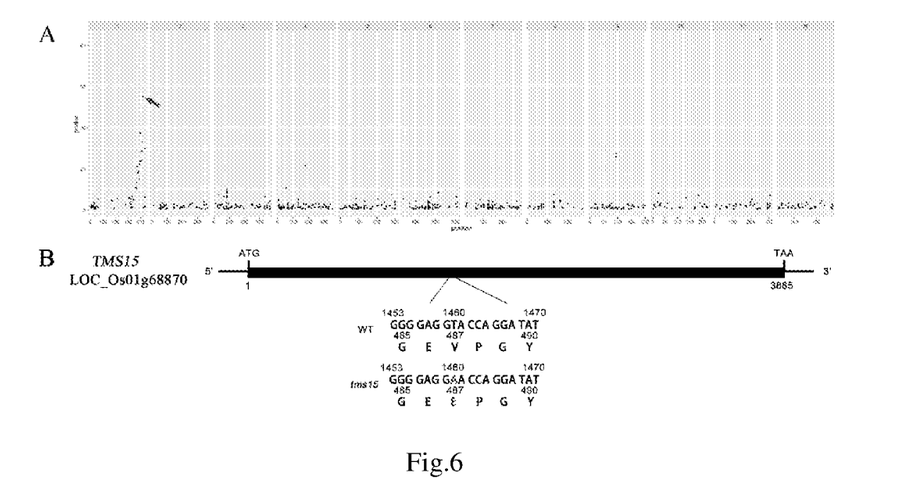
FIG. 6 shows the cloning and mutation sites of TMS15 gene.

Leaves of the $F_2$ generation segregation population plants were cut respectively, according to their fertility phenotype. Then, high-throughput sequencing was carried out on DNA extracted from the leaves. The candidate gene was located on chromosome 1 (LOC_Os01g68870/Os01g0917500) through BSA analysis. A base mutation from T to A occurred in the gene sequence (FIG. 6A). According to the rice genome annotation website, this candidate gene encodes an LRR receptor protein kinase.

5. TMS15 can Complement Thermo Sensitive Male Sterile Phenotype of Tms15 Mutant

Figure 7:
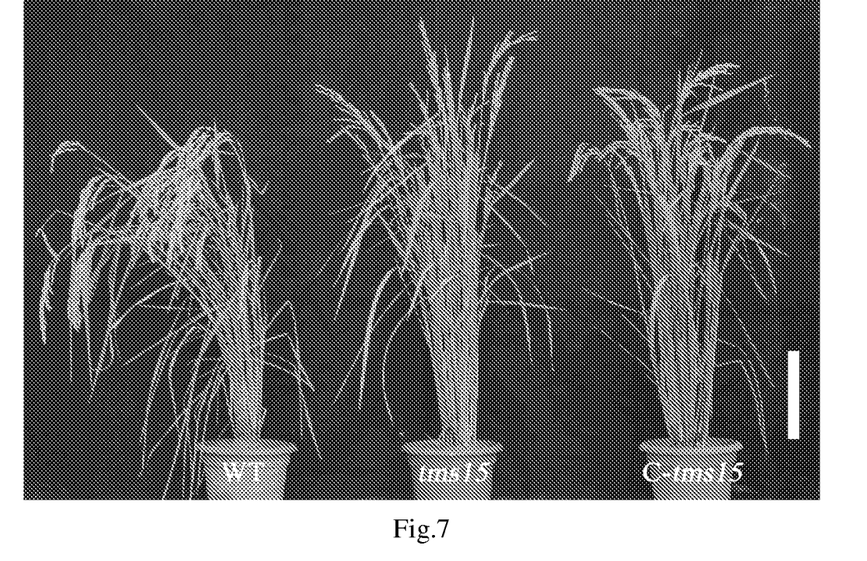
FIG. 7 shows plant phenotype of TMS15 the gene of which is complementary with tms15 mutant.
Figure 8:
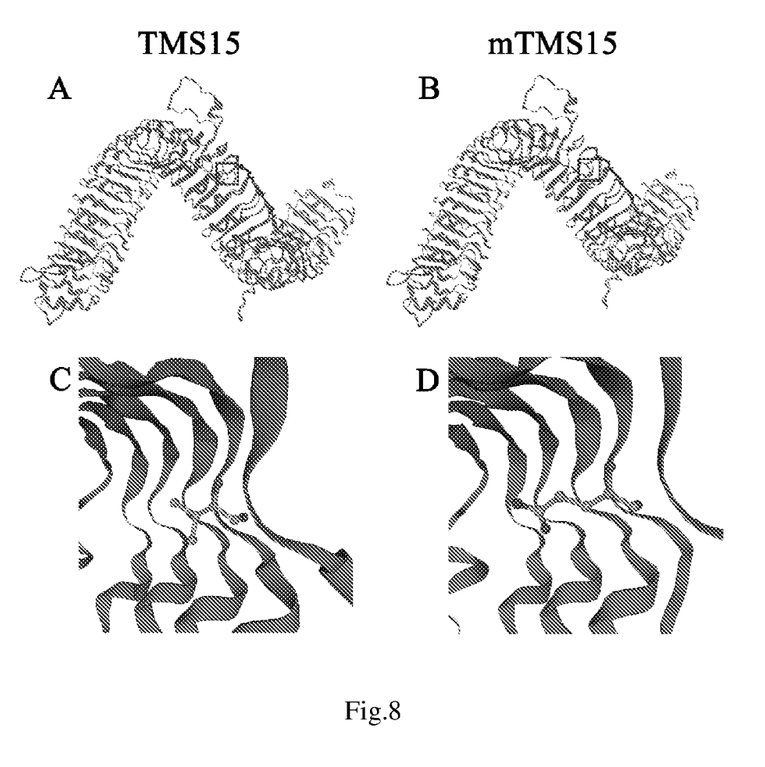
FIG. 8 shows a LRR domain protein structure and mutant amino acid sites of TMS15 in wild type and tms15 mutant, wherein region A shows three-dimensional structure of TMS15-LRR protein in wild type; region B shows three-dimensional structure of mTMS15-LRR protein in the mutant; region C shows $487^{th}$ amino acid site of TMS15 in wild type; region D shows the $487^{th}$ amino acid site of mTMS15 in the tms15 mutant. The box in the Figure indicates the position of the $487^{th}$ amino acid in the three-dimensional structure of the protein.

In order to confirm whether the targeted candidate gene is TMS15, the inventor constructed a complementary vector of TMS15. The promoter and gene sequence of LOC_Os01g68870 in DNA template of wild-type plant were amplified together and connected to the NOS tag vector. A constructed plasmid was transferred into *Agrobacterium tumefaciens* EHA105. The desired transgenic plant was finally obtained by infecting the callus which were obtained by induced tms15 in to seeds. T-DNA insertion and TMS15 background identification were carried out on these transgenic plants, and obtaining two NOS tagged transgenic complementary plants with TMS15 homozygous background. After the high-temperature phenotype verification of the transgenic complementary plants, it was found that the transgenic plants could restore fertility of tms15 mutant plants, which are sterile under high-temperature conditions (FIG. 7). So this gene is the target gene TMS15.

6. The Expression of TMS15 is Increased by Induction of Low Temperature

Figure 9:
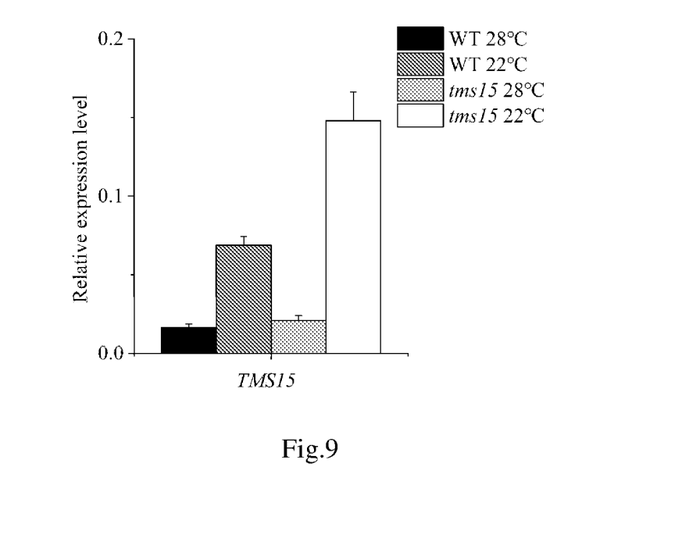
FIG. 9 shows expression amount of TMS15 in WT and plant containing tms15 at different ambient temperatures.

In order to make sure whether the thermo-sensitive effect of tms15 mutant is caused by the change in the expression of TMS15 gene itself, the inventor treated tms15 mutant plants and Wild type plants at different temperatures, and extracted RNA from spikelets less than 2 mm in length when they were booting. Reverse transcribing the RNA into cDNA, and the cDNA was used as a template for qRT-PCR experiment. In anthers of the tms15 mutant plants treated with high temperature, the expression of TMS15 gene itself had no significant change compared with Wild type plants. However, in the anthers of Wild type plants and tms15 mutant plants treated with low temperature, the expression amount of TMS15 gene is higher than that of Wild type plants and tms15 mutant plants treated with high temperature. And the expression amount of TMS15 gene in the anthers of tms15 mutant plants is nearly twice higher than that of Wild type plants (as shown in FIG. 9). These results show that the expression of TMS15 gene is induced by temperature, and the decrease of ambient temperature increases the expression of TMS15 gene. In tms15, the increase of this expression is more obvious.

Molecular Mechanism of TMS15 Gene Mutation Leading to Thermo Sensitive Male Sterility in Plants LRR RLKs mainly generate signals through the combination of their extracellular domains with different ligand proteins. The signals pass through the transmembrane domain and then pass to the phosphorylation kinase region. Kinases perform specific biological functions through phosphorylation or dephosphorylation of downstream action factors. Extracellular domains of Leucine rich repeat structure (LRR) of LRR RLKs accept different ligands through different combination manners, realizing the diversity of regulatory functions and the accuracy of regulatory space-time (Referring to Yan Feng et al., 2009).

Figure 10:
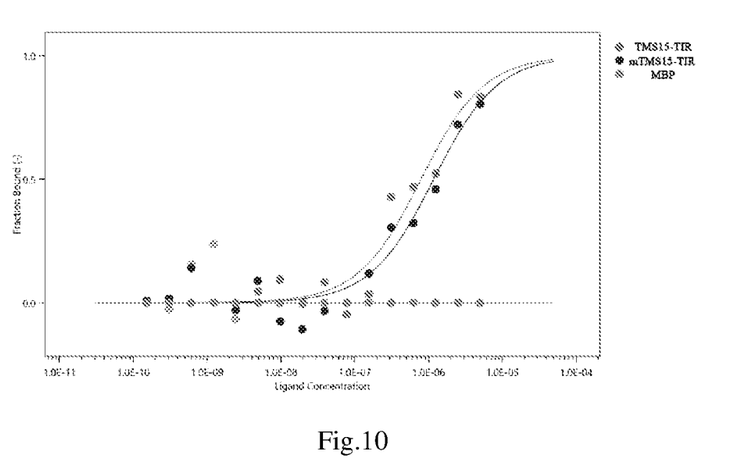
FIG. 10 shows results of microthermal swimming experiment of TMS15-TIR, mTMS15-TIR and their ligand proteins.

In the research of the invention, it is found that $1460^{th}$ base of TMS15 in the LRR coding section mutates from T to A, leading to the disorder of anther development timing, excessive proliferation of microspore mother cells, and severe vacuolization of tapetum cells of corresponding plants, which leads to pollen abortion of the plants under high temperature. Previous reports have shown that the interaction region between EMS1 and its ligand TPD1 in *Arabidopsis* is located in the 116 amino acid region of LRR. Through the comparison of amino acid sequences, it is found that the amino acid mutation site in tms15 is located in the interaction region between TMS15 and the ligand protein OsTDL1A. The change of a base at this site makes the hydrophobic amino acid—valine originally coded here become a more hydrophilic one, i.e., glutamic acid. Microthermal swimming experiments show that the replacement of this amino acid may lead to a weaker binding ability of the LRR region of TMS15 to the OsTDL1A (as shown in FIG. 10), The stability of the dimer structure formed by the LRR region of TMS15 and the OsTDL1A is reduced. Therefore, it is speculated that under the high temperature environment, the temperature rise makes the stability of the protein dimer worse than that of the wild type, which affects the process of interaction between TMS15 and OsTDL1A, interferes with the phosphorylation or dephosphorylation effect of the phosphorylation kinase domain on downstream factors, and finally leads to plant sterility. A test on the expression of transcription factors related to tapetum development and functional genes related to sporopollen synthesis in the downstream shows that their expression in tms15 under high temperature is regulated down as compared with that in wild type, especially the expression of CYP703A3 and DPW, two functional genes involved in sporopollen synthesis in the downstream, was seriously regulated down. It shows that high temperature affects the dimer of mTMS15 and OsTDL1A to transmit phosphorylation signal to the downstream normally. Through the cascade effect of genetic pathway, the expression of downstream functional genes is seriously reduced, and finally leads to the phenotype of tms15 high temperature sterility.

2. Molecular Mechanism of Fertility Restoration of Tms15 Mutant at Low Temperature The results of the study of the invention show that the expression amount of TMS15 gene in wild type plants and tms15 mutant plants under low temperature environment is significantly higher than that under high temperature. Since the tms15 mutant is caused by point mutation, its mutant protein's function preserves in some extent. Therefore, it is speculated that in the tms15 mutant plants, the expression of mTMS15 is increased under low temperature, so that more mTMS15 proteins on the membrane have greater probability to interact with its ligand OsTDL1A, thus alleviating the defect of the weak binding ability of mTMS15 and OsTDL1A, realizing sufficient phosphorylation or dephosphorylation of downstream signal factors, and completing the normal signal transmission process. Low temperature may enhance the expression of downstream transcription factors and functional genes by increasing the expression of TMS15 in tms15 mutants, and then accumulate the amount of protein required for these genes to perform biological functions, finally restoring the fertility of tms15 mutants.

3. TMS15 Gene has the Potential to be Used in Cross Breeding Production

At present, the photo thermo sensitive genic male sterile lines, which are widely used in breeding, most of their photo thermo sensitive sites come from Annong S-1 (AnS-1) and Nongken 58S (NK58S) (Zhang Huali et al., 2015). AnS-1 is a very typical indica TGMS line. According to previous studies, it is found that AnS-1 is mainly affected by high temperature from the formation of microspore mother cells to the end of meiosis (Liu Aimin and Li Bihu, 1996). TMS15 is a key factor determining tapetal differentiation and sporogenous cell proliferation during early anther's development, and its fertility is affected by high temperature earlier than the existing light thermo-sensitive genes. We can construct double mutants of them by hybridize with some thermo-sensitive lines that are widely used in breeding, so as to prolong the sensitive period of fertility transformation, obtain thermo-sensitive genic male sterile lines with lower fertility transformation temperature, reduce the risk of thermo-sensitive genic male sterile lines facing low temperature surge during seed production, and improve the stability of hybrid breeding.

The same thermo-sensitive locus will have different fertility sensitive temperature in different varieties, which may be caused by the different expression of genes affected by temperature in the genetic background of each variety, While studying the molecular mechanism of TMS15 gene, TMS15 gene is introduced into indica rice varieties that are widely used in production. Through recurrent hybridization, it is expected to obtain a thermo-sensitive male sterile line with better fertility recovery temperature than the existing thermo-sensitive male sterile lines and apply it to hybrid rice production.

The invention realizes the fast creation of a thermo sensitive genic male sterile line rice by chemical mutagenesis, obtains some photo thermo sensitive rice plants controlled by a new thermo sensitive male sterile site like tms15, introduces them into different *japonica* rice backgrounds, and selects thermo sensitive genic male sterile lines with lower critical temperature from them, which enriches the sterile line resources of two-line hybrid *japonica* rice.

It should be noted that the plant materials in the invention are cultivated in fertile soil under the following conditions: high temperature and low temperature treatment is performed in glass greenhouse and artificial intelligence lighting room. The high temperature treatment temperature is generally in summer or in an environment with an average temperature greater than 28° C., and the low temperature treatment temperature is generally in autumn or in an environment with an average temperature of 22-24.5° C., and the light source is natural.

Figure 11:
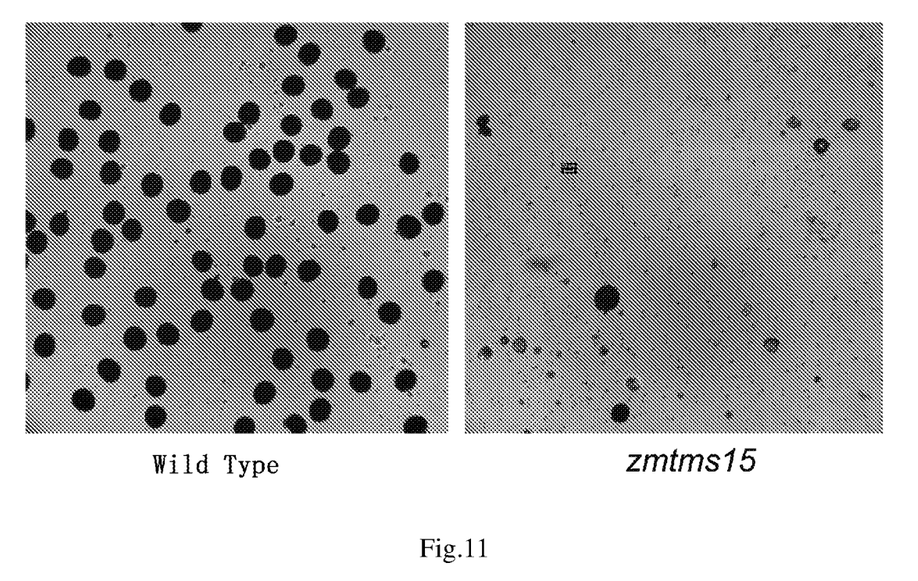
FIG. 11 shows comparison of pollen fertility between wild type maize and maize which have been introduced into the mutant tms15.

It should be noted that although the above detailed description takes rice as an example, the applicant has also performed single base editing operations on monocotyledon plants such as corn by using Crispr Cas9 guided ABE system, and performed single base mutation at the corresponding site of corn TMS15. Preliminary experiments show that the mutant also has the effectiveness of thermosensitive sterility (as shown in FIG. 11). Therefore, the plants of the invention are not limited to rice.

Those skilled in the art should understand that the above embodiments are only an explanation of the schematic implementation mode of the invention, not a limitation of the scope of the invention. The details in the embodiments do not constitute a limitation on the scope of the invention.

What is claimed is:

1. A plant thermo-sensitive male sterile gene mutant tms15, wherein nucleotide sequence of the plant thermo-sensitive male sterile gene mutant tms15 is SEQ ID No. 1.

2. An expression vector containing the plant thermo-sensitive male sterile gene mutant tms15 of claim 1.

3. A transgenic seed, wherein genome of said transgenic seed comprises the plant thermo-sensitive male sterile gene mutant tms15 of claim 1.

4. A method for cultivating a fertility restorable plant whose pollen development is affected by temperature, wherein the method includes introducing the plant thermo-sensitive male sterile gene mutant tms15 into plant seed cells, and using the plant seeds to conduct plant cultivation.

5. A method for regulating thermo-sensitive fertility traits of plants, wherein the method comprises: replacing TMS15 gene in wild type plants with the nucleotide sequence of SEQ ID No. 1, or replacing the corresponding protein of TMS15 gene with the amino acid sequence of SEQ ID No. 2.

* * * * *